United States Patent [19]

Schally et al.

[11] 4,010,125

[45] Mar. 1, 1977

[54] [D-TRP[6]]-LH-RH AND INTERMEDIATES THEREFOR

[76] Inventors: Andrew V. Schally, 2500 Whitney Place, Apt. 319, Metairie, La. 70002; David H. Coy, 3823 B. St. Charles Ave., New Orleans, La. 70115

[22] Filed: June 12, 1975

[21] Appl. No.: 586,437

[52] U.S. Cl. .................... 260/8; 260/78 A; 260/112.5 LH; 424/177; 260/6
[51] Int. Cl.[2] ............... C07C 103/52; C08L /00
[58] Field of Search ............ 260/112.5 LH, 78 A, 260/8

[56] References Cited
UNITED STATES PATENTS 3,901,872   8/1975   McKinley et al. ........ 260/112.5 LH

*Primary Examiner*—Lewis Gotts
*Assistant Examiner*—Reginald J. Suyat
*Attorney, Agent, or Firm*—Stephen Venetianer

[57] ABSTRACT

The decapeptide [D-Trp[6]]-LH-RH, salts thereof, and intermediates used for the synthesis thereof are disclosed. The decapeptide has potent LH- and FSH-releasing hormone properties.

7 Claims, No Drawings

[D-TRP⁶]-LH-RH AND INTERMEDIATES THEREFOR

The invention described herein was made in the course of work under a grant or award from the Department of health, Education and Welfare.

BACKGROUND OF THE DISCLOSURE a. Field of the Invention

This invention relates to the decapeptide (pyro)Glu-His-Trp-Ser-Tyr-D-Trp-Leu-Arg-Pro-Gly-NH$_2$, salts thereof and intermediates for the synthesis thereof.

The decapeptide of this invention also is called L-pyroglutamyl-L-histidyl-L-tryptophyl-L-seryl-L-tyrosyl-D-tryptophyl-L-leucyl-L-arginyl-L-prolyglycinamide and may be designated by the abbreviation [D-Trp⁶]-LH-RH.

b. Background of the Invention

Luteinizing hormone (LH) and follicle-stimulating hormone (FSH) are both gonadotrophic hormones elaborated by the pituitary gland of humans and of animals. LH together with FSH stimulates the release of estrogens from the maturing follicles in the ovary and induces the process of ovulation in the female. In the male LH stimulates the interstitial cells and is for that reason also called interstitial cell stimulating hormone (ICSH). FSH induces maturation of the follicles in the ovary and together with LH, plays an important role in the cyclic phenomena in the female. FSH promotes the development of germinal cells in the testes of the male. Both LH and FSH are released from the pituitary gland by the action of LH- and FSH-releasing hormone, and there is good evidence that said releasing hormone is elaborated in the hypothalamus and reaches the pituitary glnd by a neurohumoral pathway, see e.g., A. V. Schally, et al., Recent Progress in Hormone Research, 24, 497 (1968).

The natural LH- and FSH-releasing hormone has been isolated from pig hypothalami and its constitution elucidated by A. V. Schally, et al., Biochem. Biophys. Res. Commun., 43, 393 and 1334 (1971), who proposed the decapeptide structure (pyro)-Glu-His-Trp-Ser-Tyr-Gly-Leu-Arg-Pro-Gly-NH$_2$.

This constitution has been confirmed by synthesis; for example, see H. Matsuo, et al., Biochem. Biophys. Res. Comm., 45, 822 (1971) and R. Geiger et al., ibid, 45, 767 (1971).

Hereinafter the natural LH- and FSH-releasing hormone is called LH-RH.

Because of the importance of LH-RH to both diagnostic and therapeutic medicine, considerable interest has been shown in the preparation of new compounds having improved properties over the natural hormone. One approach to this goal has been the replacement of an amino acid residue of LH-RH with another amino acid. Although in a few instances decapeptides containing such a replacement have been found to be more active than LH-RH, for example, [D-Ala⁶]-LH-RH, A. Arimura, et al., Endocrinology, 95, 1174 (1971) and [D-Leu⁶]-LH-RH, J. A. Vilchez-Martinez, et al., Biochem. Biophys. Res. Commun, 59, 1226 (1974), for the most part the replacement containing decapeptides have been less active.

Now it has been found that the replacement of the glycyl moeity in position 6 of LH-RH with D-tryptophan gives a compound that is much more active and longer acting than LH-RH. Such attributes of the present decapeptide have practical significance: the lesser minimum effective dose reducing side effects as well as the cost for the preparation of the compound and the longer acting property reducing the need for frequent administration.

SUMMARY OF THE INVENTION

The compounds of this invention are selected from the group consisting of (pyro-Glu-His-Trp-Ser-Tyr-D-Trp-Leu-Arg-Pro-Gly-NH$_2$ (1) or a non-toxic, pharmaceutically acceptable salt thereof, and R⁶-(pyro)-Glu-His(N$^{im}$-R⁵)-Trp-Ser(R⁴)-Tyr(R³)-D-Trp-Leu-Arg(N$^G$-R²)-Pro-Gly-R¹ (2), in which R¹ is selected from the group consisting of amino and 0- (lower alkyl), R², R³, R⁴ and R⁵ are protective groups capable of being removed by one or more chemical treatments which do not affect (pyro)-Glu-His-Trp-Ser-Tyr-D-Trp-Leu-Arg-Pro-Gly-NH$_2$ and R⁶ is hydrogen or said protective group.

With reference to R⁶-(pyro)-Glu-His(N$^{lm}$-R⁵)-Trp-Ser(R⁴)-Tyr(R³)-D-Trp-Leu-Arg(N$^G$-R²)-Pro-Gly-R¹, in a preferred embodiment R¹ is as defined herein, R² is a protective group for the N$^\delta$, N$^\omega$, and N$^{\omega'}$ nitrogen atoms of arginine selected from the group consisting of tosyl, nitro, benzyloxycarbonyl and adamantyloxycarbonyl; R³ is a protective group for the hydroxyl of tyrosine selected from the group consisting of 2-bromo-benzyloxycarbonyl, benzyl, acetyl, tosyl, benzoyl, t-butyl, tetrahydropyran-2-yl, trityl, 2,4-dichlorobenzyl and benzyloxycarbonyl; R⁴ is a protective group for the hydroxy group of serine and is selected from the group defined hereinbefore for R³; R⁵ is a protective group for the imidazole nitrogen atoms of histidine selected from the group of tosyl, dinitrophenyl, 2,2,2-trifluoro-1-benzoyloxycarbonylaminoethyl and 2,2,2-trifluoro-1-t-butyloxycarbonylaminoethyl; and R⁶ is hydrogen or an α-amino protective group selected from the group consisting of t-butyloxycarbonyl, benzyloxycarbonyl, cyclopentyloxycarbonyl, t-amyloxycarbonyl and d-isobornyl-oxycarbonyl.

A further aspect of the present invention relates to intermediates linked to a solid resin support. These intermediates are represented by the formulae:

R⁶-(pyro)-Glu-His-(N$^{1m}$-R⁵)-Trp-Ser(R⁴)-Tyr(R³)-D-Trp-Leu-Arg(N$^G$-R²)-Pro-Gly-A, R⁷-His-(N$^{1m}$-R⁵)-Trp-Ser(R⁴)-Tyr(R³)-D-Trp-Leu-Arg(N$^G$-R²)-Pro-Gly-A, R⁷-Trp-Ser(R⁴)-Tyr(R³)-D-Trp-Leu-Arg(N$^G$-R²)-Pro-Gly-A, R⁷-Ser(R⁴)-Tyr(R³)-D-Trp-Leu-Arg(N$^G$-R²)-Pro-Gly-A, R⁷-Tyr(R³)-D-Trp-Leu-Arg(N$^G$-R²)-Pro-Gly-A and R⁷-D-Trp-Leu-Arg(N$^G$-R²)-Pro-Gly-A in which R², R³, R⁴R⁵ and R⁶ are as defined herein and R⁷ is an α-amino protective group known to be useful in the art for the stepwise synthesis of polypeptides, suitable group being listed hereinafter, and A is an anchoring bond used in solid phase synthesis linked to a solid resin support. A is selected from the class consisting of:

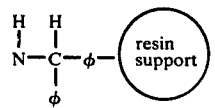 and 

DETAILS OF THE INVENTION

The term "lower alkyl" contemplates alkyl radicals containing from one to three carbon atoms and includes methyl, ethyl, propyl and isopropyl.

$N^G$ means the side chain nitrogen atoms of arginine.

$N^{1m}$ means the imidazole nitrogen atoms of histidine.

The symbol $\phi$ means "phenyl".

In general the abbreviations used herein for designating the amino acids and the protective groups are based on recommendations of the IUPAC-IUB Commission on Biochemical Nomeclature, see Biochemistry 11, 1726 (1972). For instance, t-Boc represents t-butyloxycarbonyl, Z represents benzyloxycarbonyl, Tos represents tosyl, 2-Br-Cbz represents 2-bromo-benzyloxycarbonyl and Bzl represents benzyl. The abbreviations used herein for the various amino acids are Arg, arginine; Gly, glycine; His, histidine; Leu, Leucine; Pro, proline; (pyro)-Glu, 5-oxoproline(pyroglutamic acid); Ser. serine; Trp, tryptophan; and Tyr, tyrosine. All amino acids described herein are in the L-series unless stated otherwise, i.e., D-Trp is a D-tryptophyl residue.

The polypeptide of this invention can be obtained in the form of an acid addition salt. Examples of salts are those with organic acids, e.g. acetic, lactic, succinic, benzoic, salicylic, methanesulfonic or toluenesulfonic acid, as well as polymeric acids such as tannic acid or carboxymethyl cellulose, and salts with organic acids such as hydrohalic acids, e.g. hydrochloric acid, or sulfuric acid, or phosphoric acid. If desired a particular acid addition salt is converted into another acid addition salt, e.g. a salt with a non-toxic, pharmaceutically acceptable acid, by treatment with the appropriate ion exchange resin in the manner described by R. A. Boissonnas, et al., Helv. Chim. Acta, 43, 1349 (1960). Suitable ion exchange resins are cellulose based cation exchangers, for example carboxymethylcellulose or chemically modified, cross linked dextran cation exchangers, for example, those of the sephadex C-type, and strongly basic anion exchange resins, for example those listed by J.P. Greenstein and M. Winitz in "Chemistry of the Amino Acids", John Wiley and Sons, Inc., New York and London, 1961, Vol. 2, p. 1456.

The decapeptide of this invention and its salts possess valuable, long-acting LH- and FSH-releasing hormone activity.

The valuable LH- and FSH-releasing hormone activity and long acting property of the compound of this invention are demonstrated by standard pharmacological procedures. For example, these activities can be demonstrated by tests described by A. Arimura, et al., Endocrinology, 95, 1174 (1974). More specifically, by following the procedure described therein, LH-release data obtained from rats given equal doses (50 ng, subcutaneously) show that [D-Trp$^6$]-LH-RH reaches peak activity at about two hours after dosing and that significant activity is still present up to 6 hours; whereas after an injection of LH-RH, peak activity is reached at about the 15 minute mark and no effects of the injection are observed after one hour. Also integrated levels of LH over a 6 hour period indicate that [D-Trp$^6$]-LH-RH is about 12 times more active in releasing LH-RH. FSH-release data following injections of the two compounds indicate that [D-Trp$^6$]-LH-RH is about 20 times more active than LH-RH at the same dose (50 ng).

Moreover, the activity of the compound of this invention is demonstrated readily in man.

Radioimmunoassay of serum levels of LH after intranasal administration indicates that the minimum effective dose of LH-RH is about 2.0 mg whereas an equivalent degree of activity is obtained with a 0.5 mg dose of [D-Trp$^6$]-LH-RH. In this instance the compounds are given to humans in a normal saline solution. With regard to FSH release in man comparative studies with LH-RH and [D-Trp$^6$]-LH-RH give particularly noteworthy results. Intranasal administration of up to 2.0 mg of LH-RH has little or no effect on FSH serum levels as measured by radioimmunoassay, H. G. Dahlin, et al., Horm. Metab. Res., 6, 510 (1974); however, the compound of this invention releases significant amounts of FSH, i.e., levels ranging from 0.3 to greater than 1.5 miu/ml, at 0.5 mg under the same conditions. It will be readily appreciated that a compound that is able to effectively release FSH has many therapeutic applications; see, for example, H.G. Dahlén, et al., cited above.

The LH- and FSH-releasing properties of the compound of this invention, which in turn induce ovulation in animals, make the hormone useful in veterinary practice and in animal husbandry. It is often desirable to synchronize estrus in livestock, for example, cattle, sheep or swine, either in order to be able to mate all the females in a given group with a male of the desired genetic quality, or so as to be able to perform artificial insemination on a maximum number of females, both within a comparatively short period of time. In the past, this has been done by administering to the animals and ovulation-inhibiting agent, withdrawing administration of said agent shortly before the date chosen for mating or artificial insemination, and relying either upon the natural production of LH and FSH to induce ovulation and to produce estrus or by administering gonadotrophins. However, this procedure was not entirely satisfactory because ovulation at a predetermined time occurred never in all the animals together but only in a certain proportion thereof when gonadotrophins were not used. On the other hand, the high cost of gonadotrophins and side effects encountered in their administration made this method impractical. It is now possible to obtain substantially complete synchronization of ovulation and of estrus, by treating the animals in a given group first with an ovulation inhibitor which is subsequently withdrawn, and then administering ]D-Trp$^6$]-LH-RH shortly before the predetermined period of time for mating or artificial insemination, so as to obtain ovulation and estrus within that time interval. The delay in the onset of ovulation and estrus following administration of [D-Trp$^6$]-LH-RH varies with the species of animals, and the optimal time interval has to be chosen for each species. For example, in rodents such as rats or hamsters ovulation takes place within 18 hours following administration of the decapeptide of this invention.

The method described above for obtaining ovulation and estrus within a precisely predetermined time interval, so as to be certain of a successful mating, is particularly important for breeders of race horses and of show animals, where the fees paid for the services of an exceptional male animal often amount to very considerable sums of money. [D-Trp$^6$]-LH-RH is also useful to increase the number of live births per pregnancy in livestock, for example, cattle, sheep or swine. For this purpose the decapeptide is given in a series of parenteral doses, preferably by intravenous or subcutaneous injections, in the range of 0.1 –10 mcg. per kilogram of body weight per day, 96 to 12 hours prior to expected estrus and subsequent mating. A priming injection of 1000 to 5000 iu of pregnant mares serum gonadotrophin may also be given one to four days prior to the above injection of the decapeptide. A similar treatment, with or without prior priming, is also useful for inducing puberty in farm animals.

When the decapeptide is employed for the purpose of inducing ovulation and estrus or for inducing puberty in warm-blooded animals, especially in rodents such as rats or hamsters or in livestock it is administered systemically, preferably parenterally, in combination with a pharmaceutically acceptable liquid or solid carrier. The proportion of the decapeptide is determined by its solubility in the given carrier, by the chosen route of adminstration, and by standard biological practice. For parenteral administration to animals the decapeptide is used in a sterile aqueous solution which may also contain other solutes such as buffers or preservatives, as well as sufficient pharmaceutically acceptable salts or glucose to make the solution isotonic. The dosage will vary with the form of administration and with the particular species of animal to be treated and is preferably kept at a level of from 0.1 mcg. to 10 mcg. per kilogram body weight. However, a dosage level in the range of from about 1 mcg. to about 5 mcg. per kilogram body weight is most desirably employed in order to achieve effective results.

The decapeptide may also be administered in one of the long-acting, slow-release or depot dosage forms described below, preferably by intramuscular injection or by implantation. Such dosage forms are designed to release from about 0.1 mcg. to about 10 mcg. per kilogram body weight per day. [D-Trp$^6$]-LH-RH is also useful in human medicine. For example, human chrionic gonadotrophin (HCG) which contains mainly LH and some FSH has been used for over 30 years to treat certain endocrinological disorders such as disturbances of the cycle, amenorrhea, lack of development of secondary sec characteristics, and infertility in the female, or certain cases of hypogonadism delayed puberty, cryptorchidism, and non-psychogenic impotence in the male. Lately, infertility in the human female has also been treated with human menopausal gonadotrophin (HMG) which contains mainly FSH, followed by treatment with HCG. One of the disadvantages of the treatment of infertility in the human female with HCG or with HMG followed by HCG had become apparent in that such treatment often results in superovulation and unwanted multiple births, probably because of the impossibility of giving only the exact amounts of FSH and LH which are necessary for ovulation. The administration of the decapeptide of this invention overcomes the above disadvantage, because the compound causes release of LH and FSH by the pituitary only in the exact quantities which are required for normal ovulation. For that reason the decapeptide of this invention is not only useful for the above purpose, but it is equally useful in the human female in the treatment of disturbances of the cycle, of amenorrhea, of hypogonadism, and of lack of development of secondary sex characteristics.

Furthermore, the decapeptide of this invention is useful in contraception. For example, when the decapeptide is administered to a human female early in the menstrual cycle LH is released at that time and causes premature ovulation. The immature ovum is either not capable of being fertilized, or, if fertilization should nevertheless have taken place, it is highly unlikely that the fertilized ovum will become implanted because the estrogen-progestin balance required to prepare the endometrium is not present and the endometrium is not in the condition necessary for implantation. On the other hand, when the decapeptide is adminstered towards the end of the cycle the endometrium is disrupted and menstruation takes place.

In addition, the decapeptide of this invention is also useful in contraception by the "rhythm" method, which has always been relatively unreliable because of the impossibility of predetermining ovulation in the human female with the required degree of accuracy. Administration of the decapeptide at mid-cycle, i.e. at about the normally expected time for ovulation, induces ovulation shortly thereafter and makes the rhythm method both safe and effective.

The decapeptide is also useful as a diagnostic tool for distinguishing between hypothalamic and pituitary malfunctions or lesions in the human female. When administering the decapeptide to a patient suspected of such malfunctions or lesions and a rise in the level of LH is subsequently observed there is good indication to conclude that the hypothalamus is the cause of the malfunction and that the pituitary is intact. On the other hand, when no rise in circulating LH is seen following the administration of the decapeptide a diagnosis of pituitary malfunction or lesion can be made with a high degree of confidence.

In the human male, administration of decapeptide provides the amounts of LH (or ICSH) and of FSH necessary for normal sexual development in cases of hypogonadism or delayed puberty, and is also useful in the treatment of cryptorchidism. Furthermore, the FSH released by the administration of the decapeptide stimulates the development of germinal cells in the testes, and the decapeptide is useful in the treatment of psychogenic and nonpsychogenic impotence.

When the decapeptide, preferably in the form of an acid addition salt, is employed in human medicine, it is administered systemically, either by intravenous, subcutaneous, or intramuscular injection, or by sublingual, nasal, or vaginal administration, in compositions in conjunction with a pharmaceutically acceptable vehicle or carrier.

For administration by the nasal route as drops or spray it is preferred to use the decapeptide in solution in a sterile aqueous vehicle which may also contain other solutes such as buffers or preservatives, as well as sufficient quantities of pharmaceutically acceptable salts or of glucose to make the solution isotonic. Doses by the intranasal route range from 0.1 to 50 mcg/kg, or preferably 0.5 to 10 mcg/kg.

The decapeptide may also be administered as nasal or vaginal powders or insufflations. For such purposes the decapeptide is adminstered in finely divided solid form together with a pharmaceutically acceptable solid carrier, for example a finely divided polyethylene glycol ("Carbowax 1540"), finely divided lactose, or preferably for vaginal administration, very finely divided silica ("Cab-O-Sil"). Such compositions may also contain other excipients in finely divided solid form such as preservatives, buffers, or surface active agents.

For sublingual or vaginal administration it is preferred to formulate the decapeptide in solid dosage forms such as sublingual tablets or vaginal inserts or suppositories with sufficient quantities of solid excipients such as starch, lactose, certain types of clay, buffers, and lubricating, disintegrating, or surface-active agents, or with semi-solid excipients commonly used in the formulation of suppositories. Examples of such excipients are found in standard pharmaceutical texts, e.g. in Remington's Pharmaceutical Sciences, Mack Publishing Company, Easton, Pa., 1970.

The dosage of the decapeptide will vary with the form of administration and with the particular patient under treatment. Generally, treatment is initiated with small dosages substantially less than the optimum dose of the compound. Thereafter, the dosage is increased by small increments until the optimum effect under the circumstances is reached. In general, the decapeptide obtained by the process is most desirably administered at a concentration level that will generally afford effective release of LH and of FSH without causing any harmful or deleterious side effects, and preferably at a level that is in a range of from about 0.1 mcg. to about 100 mcg. per kilogram body weight, although as aforementioned variations will occur. However, a dosage level that is in the range of from about 0.5 mcg to about 5 mcg per kilogram body weight is most desirably employed in order to achieve effective results.

It is often desirable to administer the decapeptide continuously over prolonged periods of time in long-acting, slow-release, or depot dosage forms. Such dosage forms may either contain a pharmaceutically acceptable salt of the compound having a low degree of solubility in body fluids, for example one of those salts described below, or they may contain the decapeptide in the form of a water-soluble salt together with a protective carrier which prevents rapid release. In the latter case, for example, the decapeptide may be formulated with a non-antigenic partially hydrolyzed gelatin in the form of a viscous liquid; or it may be absorbed on a pharmaceutically acceptable solid carrier, for example zinc hydroxide, and may be administered in suspension in a pharmaceutically acceptable liquid vehicle; or the decapeptide may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or nonaqueous pharmaceutically acceptable liquid vehicles, preservatives, or surfactants. Examples of such formulations are found in standard pharmaceutical texts, e.g. in Remington's Pharmaceutical Sciences, cited above. Long-acting, slow-release preparations of the decapeptide may also be obtained by microencapsulation in a pharmaceutically acceptable coating material, for example gelatine, polyvinyl alcohol or ethyl cellulose. Further examples of coating materials and of the processes used for microencapsulation are described by J. A. Herbig in "Encyclopedia of Chemical Technology", Vol. 13, 2nd Ed., Wiley, New York, 1967, pp. 436–456. Such formulations, as well as suspensions of salts of the decapeptide which are only sparingly soluble in body fluids, are designed to release from about 0.1 mcg to about 50 mcg of the hormone per kilogram body weight per day, and are preferably administered by intramuscular injection. Alternatively, some of the solid dosage forms listed above, for example certain sparingly water-soluble salts or dispersions in or adsorbates on solid carriers of salts of the decapeptide, for example dispersions in a neutral hydrogel of a polymer of ethylene glycol methacrylate or similar monomers cross-linked as described in U.S. Pat. No. 3,551,556 may also be formulated in the form of pellets releasing about the same amounts as shown above and may be implanted subcutaneously or intramuscularly.

Alternatively, slow-release effects over prolonged periods of time may also be obtained by administering the decapeptide obtained by the process of this invention as an acid addition salt in an intra-vaginal device or in a temporary implant, for example a container made of a non-irritating silicone polymer such as a polysiloxane, e.g. "Silastic", or of a neutral hydrogel of a polymer as described above, possessing the required degree of permeability to release from about 0.1 mcg. to about 50 mcg per kilogram body weight per day. Such intra-vaginal or implant dosage forms for prolonged administration have the advantage that they may be removed when it is desired to interrupt or to terminate treatment.

PROCESS

In selecting a particular side chain protective group to be used in the synthesis of the present decapeptide, the following rules should be followed: (a) the protective group must be stable to the reagent and under the reaction conditions selected for removing the α-amino protective group at each step of the synthesis, (b) the protective group must retain its protecting properties (i.e., not be split off under coupling conditions), and (c) the side chain protective group must be removable upon the completion of the synthesis containing the desired amino acid sequence under reaction conditions that will not alter the peptide chain.

With reference to $R^7$, suitable protective groups include (1) aliphatic urethan protective groups illustrated by t-butyloxycarbonyl, diisopropylmethoxycarbonyl, biphenylisopropyloxycarbonyl, isopropyloxycarbonyl, t-amyloxycarbonyl, ethoxycarbonyl, allyloxycarbonyl; (2) cycloalkyl urethan type protective groups illustrated by cyclopentyloxycarbonyl, adamantyloxycarbonyl, d-isobornyloxycarbonyl, cyclohexyloxycarbonyl; nitrophenylsulfenyl, tritylsulfenyl, α,α-dimethyl-3,5-dimethoxybenzyloxycarbonyl and trityl. The preferred α-amino protective group for $R^7$ are selected from the group consisting of t-butyloxycarbonyl, cyclopentyloxycarbonyl, t-amyloxycarbonyl, d-isobornyloxycarbonyl, o-nitrophenylsulfenyl, biphenylisopropyloxycarbonyl, and α,α-dimethyl-3,5-dimethoxybenzyloxycarbonyl.

The decapeptide of this invention is prepared using solid phase synthesis. The synthesis is commenced from the C-terminal end of the peptide using an α-amino protected resin. Such a starting material is prepared by attaching an α-amino protected glycine to a benzhydrylamine resin, a chloromethylated resin or a hydroxymethyl resin, the former being preferred. The preparation of a benzhydrylamine resin is described by P. Rivaille, et al., Helv. Chim. Acta, 54, 2772 (1971) and the preparation of the hydroxymethyl resin is described by M. Bodanszky and J. T. Sheehan, Chem. Ind (London) 38, 1597 (1966). A chloromethylated resin is commercially available from Bio Rad Laboratories, Richmond, California. In using the benzhydrylamine resin an amide anchoring bond is formed with the α-amino protected glycine as follows:

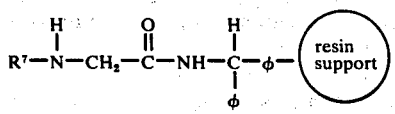

This permits the C-terminal amide function to be obtained directly after the amino acid sequence in the synthesis is completely cleaving off the resin support of the linked peptide to form the glycine amide at the C-terminal portion of the desired decapeptide. In this instance the use of hydrogen fluoride for cleaving off the resin support also removes the side chain protective groups to give the decapeptide of this invention.

When the other resins are used, the anchoring bond is the benzylester group as illustrated hereinbefore. In this instance a convenient procedure for converting the linked protected peptide to the C-terminal amide is to ammonolize the protected peptide off the resin and then remove the protective groups of the resulting amide by treatment with sodium and liquid ammonia or by hydrogen fluoride cleavage. An alternative procedure would be to cleave by transesterification with a lower alkanol, preferably methanol or ethanol, in the presence of triethylamine and then convert the resulting ester into an amide and subsequently deprotect as described above. See also J. M. Steward and J. D. Young, "Solid Phase Peptide Synthesis", W. H. Freeman & Co., San Francisco, 1969, pp. 40–49.

More specifically, in an embodiment of the present invention an α-amino protected glycine, preferably t-butyloxycarbonylglycine, is coupled to benzhydrylamine resin with the aid of the carboxyl group activating compound, preferably, dicyclohexylcarbodiimide. Following the coupling of the α-amino protected glycine to the resin support, the α-amino protecting group is removed such as by using trifluoroacetic acid in methylene chloride, trifluoroacetic acid alone or hydrochloric acid in dioxane. The deprotection is carried out at a temperature between about 0° C and room temperature. Other standard cleaving reagents and conditions for removal of specific α-amino protecting groups may be used as described by E. Schroder and K. Lubke, "The Peptides", Vol. 1, Academic Press, New York, 1965, pp. 72–75. After removal of the α-amino protecting group, the remaining α-amino protected amino acids are coupled step-wise in the desired order to obtain the decapeptide. Each protected amino acid is introduced into the solid phase reactor in about a three-fold excess and the coupling is carried out in a medium of methylene chloride or mixtures of dimethylformamide in methylene chloride. In cases where incomplete coupling occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser, et al., Analyt. Biochem. 34, 595 (1970).

After the desired amino acid sequence has been synthesized, the peptide is removed from the resin support by treatment with a reagent such as hydrogen fluoride which not only cleaves the peptide from the resin but also cleaves all remaining side chain protecting groups and the α-amino protecting group (if present) on the pyroglutamic acid residue to obtain directly the decapeptide in the case where the benzhydrylamine resin was used.

Where a chloromethylated resin is used the peptide may be separated from the resin by transesterification with a lower alkanol, preferably methanol or ethanol, after which the recovered product is chromatographed on silica gel and the collected fraction subjected to treatment with ammonia to convert the lower alkyl ester, preferably the methyl or ethyl ester, to the C-terminal amide. The side chain protecting groups are then cleaved by procedures described above, for example by treatment with sodium in liquid ammonia or by hydrogen fluoride.

Although a solid phase synthesis of the decapeptide of this invention is disclosed herein, the preparation of the decapeptide also can be realized by classical methods. For example, by following the procedure of H. U. Immer et al., U.S. Pat. No. 3,853,108, issurd September 10, 1974 but substituting Ser-Tyr-D-Trp-NHNHBoc for Ser-Tyr-Gly-NHNHBoc, the decapeptide also is obtained (via (pyro)-Glu-His-Trp-Ser-Tyr-D-Trp-NHNH$_2$).

The following Examples illustrate further this invention.

EXAMPLE 1

L-Pyroglutamyl-L-histidyl(tosyl)-L-tryptophyl-L-seryl(benzyl-L-tyrosyl(2-bromo-benzyloxycarbonyl)-D-tryptophyl-L-leucyl-L-arginyl(tosyl)-L-prolylglycyl-benzhydrylamine resin (R$^6$-(pyro)-Glu-His-(N$^{lm}$-R$^5$)-Trp-Ser(R$^4$)-Tyr(R$^3$)-D-Trp-Leu-Arg(N$^G$-R$^2$)-Pro-Gly-A; R$^2$ = Tos, R$^3$ = 2-Br-Cbz, R$^4$ = Bzl, R$^5$ = Tps, R$^6$ = H and A = benzhydrylamine resin).

Benzhydrylamine resin (1.25 g, 1.0 mmole) is placed in the reaction vessel of a Beckman Model 990 automatic peptide synthesizer programmed to carry out the following wash cycle: (a) methylene chloride; (b) 33% trifluoroacetic acetic in methylene chloride (2times for 2.5 and 25 minutes each); (c) methylene chloride; (d) ethanol; (e) chloroform; (f) 10% triethylamine in chloroform (2 times for 25 minutes each); (g) chloroform; (h) methylene chloride.

The washed resin is then stirred with t-butyl-oxycarbonyl glycine (525 mg, 3.0 mmoles) in methylene chloride and dicyclohexylcarbodiimide (3.0 mmoles) is added. The mixture is stirred at room temperature (22°–25° C) for 2 hours and the amino acid resin is then washed successively with methylene chloride (3 times), ethanol (3 times), and methylene chloride (3 times). The attached amino acid is deprotected with 33% trifluoroacetic acid in methylene chloride (2 times for 2.5 and 25 minutes each and then steps (c) through (h) as described in the above wash cycle are performed.

The following amino acids (3.0 mmoles) are then coupled successively by the same cycle of events: t-Boc-L-proline; t-Boc-L-arginine(Tos); t-Boc-L-leucine; t-boc-D-tryptophan; t-boc-L-tyrosine (2-Br-Cbz); t-Boc-L-serine(Bzl); t-Boc-L-tryptophan; t-Boc-L-histidine(Tos); L-(pyro)-glutamic acid.

The completed decapeptide resin is washed with methylene chloride (3 times) followed by methanol (3 times) and dried under reduced pressure whereupon 98% of the theoretical weight gain is obtained.

The benzhydrylamine resin used in this example is a commercially available resin (1% cross linked, Bachem Inc., Marina del Rey, California).

EXAMPLE 2

L-Pyroglutamyl-L-histidyl-L-tryptophyl-L-seryl-L-tyrosyl-D-tryptophyl-L-leucyl-L-arginyl-L-prolyl-glycinamide Removal of protecting groups and cleavage of the decapeptide from the resin is carried out by treatment of 1.0 g of material with hydrogen fluoride (24 ml) and anisole (6 ml) at 0° C for 30 minutes. The hydrogen fluoride is removed under reduced pressure and the anisole removed by washing with ethyl acetate.

The crude peptide is purified by gel filtration on a column (2.5 × 100 cm) of Sephadex G-25 (a fine grade, chemically modified cross-linked dextran) by elution with 2 molar acetic acid and fractions shown to contain a major peak by UV absorption at 280 nm were pooled and evaporated to dryness.

The residual oil was applied to a column (2.5 × 100 cm) of Sephadex G-25 (fine), previously equilibrated with the lower phase followed by the upper phase of n-butanol; acetic acid; water (4:1:5) solvent system. Elution with the upper phase gives a major peak and material from this area was subjected to elution on a column (1.4 × 94 cm) of carboxymethyl cellulose according to the conditions described by D. H. Coy, et al., J. Med. Chem., 16, 1140 (1973). Appropriate fractions (1050 –1190 ml), after lyophilization to constant weight, gave D-Trp$^6$-LH-RH as a white, fluffy powder (80 mg); $[\alpha]_D^{23}$ −58.8° (c = 0.33, IN HOAc).

The product was homogeneous by thin layer chromatography in four separate solvent systems when loads of 20–30 mcg were applied and spots visualized by exposure to iodine vapour followed by Ehrlich reagent. The following Rf values were obtained:

1-butanol: acetic acid: water (4:1:5: upper phase), 0.25; ethyl acetate: pyridine: acetic acid: water (5:5:1:3), 0.63: 2-propanol: 1 M acetic acid (2:1), 0.38; 1-butanol: acetic acid: water: ethyl acetate (1:1:1:1), 0.51.

Amino acid analysis gave: Glu, 1.08; His, 0.95; Trp, 2.00; Ser, 0.94; Tyr, 0.97; Leu, 0.93; Arg, 0.98; Pro, 1.00; Gly, 1.02; NH$_3$, 1.03.

We claim:

1. A compound of the formula R$^6$-(Pyra)-Glu-His(N$^{im}$-R$^5$)-Trp-Ser(R$^4$)-Tyr(R$^3$)-D-Trp-Leu-Arg(N$^G$-R$^2$)-Pro-Gly-R$^1$ in which R$^1$ is amino or 0-(lower alkyl), R$^2$ is a protective group for the N$^\delta$, N$^\omega$, and N$^{\omega'}$ nitrogen atoms of arginine selected from the group consisting of tosyl, nitro, benzyloxycarbonyl and adamantyloxycarbonyl;

R$^3$ is a protective group for the hydroxyl of tyrosine selected from the group consisting of 2-bromobenzyloxycarbonyl, benzyl, acetyl, tosyl, benzoyl, t-butyl, tetrahydropyran-2-yl, trityl, 2,4-dichlorobenzyl and benzyloxycarbonyl;

R$^4$ is a protective group for the hydroxyl group of serine and is selected from the group defined hereinbefore for R$^3$;

R$^5$ is a protective group for the imidazole nitrogen atoms of histidine selected from the group of dinitrophenyl, tosyl, 2,2,2-trifluoro-1-benzoyloxycarbonylaminoethyl and 2,2,2-trifluoro-t-butyloxycarbonylaminoethyl; and R$^6$ is hydrogen or an α-amino protective group selected from the group consisting of t-butyloxycarbonyl, benzyloxycarbonyl, cyclopentyloxycarbonyl, t-amyloxy-carbonyl and d-isobornyloxycarbonyl.

2. The compound of claim 1 in which R$^1$ is amino.

3. The compound of claim 1 wherein R$^1$ is amino, R$^2$ is tosyl, R$^3$ is 2-bromo-benzyloxycarbonyl, R$^4$ is benzyl, R$^5$ is tosyl and R$^6$ is hydrogen.

4. The compound which is L-pyroglutamyl-L-histidyl-L-tryptophyl-L-seryl-L-tyrosyl-D-tryptophyl-L-leucyl-L-arginyl-L-prolylglycinamide, or a non-toxic, pharmaceutically acceptable addition salt thereof.

5. A compound selected from the group consisting of R$^6$-(pyro)-Glu-His-(N$^{im}$-R$^5$)-Trp-Ser(R$^4$)-Tyr(R$^3$)-D-Trp-Leu-Arg(N$^G$-R$^2$)-Pro-Gly-A, R$^7$-His(N$^{im}$-R$^5$)-Trp-Ser(R$^4$)-Tyr-(R$^3$)-D-Trp-Leu-Arg(N$^G$-R$^2$)-Pro-Gly-A, R$^7$-Trp-Ser(R$^4$)-tyr-(R$^3$)-D-Trp-Leu-Arg(N$^G$-R$^2$)-Pro-Gly-A, R$^7$-Ser(R$^4$)-Tyr-(R$^3$)-D-Trp-Leu-Arg(N$^G$-R$^2$)-Pro-Gly-A, R$^7$-Tyr(R$^3$)-D-Trp-Leu-Arg-(N$^G$-R$^2$)-Pro-Gly-A, and R$^7$-D-Trp-Leu-Arg(N$^G$-R$^2$)-Pro-Gly-A, in which [R$^2$, R$^3$, R$^4$ and R$^5$ are protective groups capable of being removed by one or more chemical treatments which do not effect (pyro)-Glu-His-Trp-Ser-Tyr-D-Trp-Leu-Arg-Pro-Gly-NH$_2$,] R$^2$ is a protective group for the N$^\delta$, N$^\omega$, and N$^{\omega'}$ nitrogen atoms of arginine selected from the group consisting of tosyl, nitro, benzyloxycarbonyl and adamantyloxycarbonyl;

R$^3$ is a protective group for the hydroxyl of tyrosine selected from the group consisting of 2-bromo-benzyloxycarbonyl, benzyl, acetyl, tosyl, benzoyl, t-butyl, tetrahydropyran-2-yl, trityl, 2,4-dichlorobenzyl and benzyloxycarbonyl;

R$^4$ is a protective group for the hydroxyl group of serine and is selected from the group defined hereinbefore for R$^3$;

R$^5$ is a protective group for the imidazole nitrogen atoms of histidine selected from the group of dinitrophenyl, tosyl, 2,2,2-trifluoro-1-benzoyloxycarbonylaminoethyl and 2,2,2-trifluoro-t-butyloxycarbonylaminoethyl; and R$^6$ is hydrogen or an α-amino protective group and R$^7$ is an α-amino protective group, and A is selected from the class consisting of:

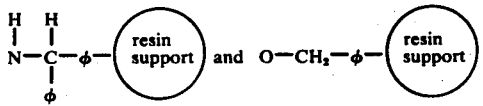

6. The compound according to claim 5 in which A is a benzhydrylamine resin.

7. The compound of claim 5 having the formula R$^6$-(pyro)-Glu-His-(N$^{im}$-R$^5$)-Trp-Ser(R$^4$)-Tyr(R$^3$)-D-Trp-Leu-Arg(N$^G$-R$^2$)-Pro-Gly-A in which R$^2$ is tosyl, R$^3$ is 2-bromo-benzyloxycarbonyl, R$^4$ is benzyl, R$^5$ is tosyl, R$^6$ is hydrogen and A is benzhydrylamine resin.

* * * * *